US United States Patent [19] [11] 4,401,455
Sikorski et al. [45] Aug. 30, 1983

[54] ESTER DERIVATIVES OF N-ALKYLTHIO-N-CYCLOALKYL THIO-N-PHOSPHONOMETHYLGLYCINE AND HERBICIDAL METHODS USING SAME

[75] Inventors: James A. Sikorski, West Lafayette, Ind.; Mary A. Hoobler, Creve Coeur, Mo.

[73] Assignee: Monsanto Company, St. Louis, Mo.

[21] Appl. No.: 309,326

[22] Filed: Oct. 5, 1981

[51] Int. Cl.³ .................. A01N 57/22; C07F 9/32
[52] U.S. Cl. ............................ 71/087; 260/941; 260/968
[58] Field of Search ............... 260/941, 968; 71/87

[56] References Cited

U.S. PATENT DOCUMENTS 4,120,689 10/1978 Dutra .................................. 71/86
4,252,554 2/1981 Dutra et al. ....................... 260/940

OTHER PUBLICATIONS

Senning, "Topics in Sulfur Chemistry," vol. 1, (1977), p. 15.
Jun-ichi Ohishi, A New Cyclopropanation Method Mediated by Organosulfur Compounds (1980), Synthesis 9, pp. 690–691.

Primary Examiner—Anton H. Sutto
Attorney, Agent, or Firm—Arnold H. Cole; Howard C. Stanley; Gordon F. Sieckmann

[57] ABSTRACT

This invention relates to novel ester derivatives of N-alkylthio and N-cycloalkyl thio-N-phosphonomethylglycine which are useful as herbicides and to a process for producing the same. This invention further relates to herbicidal compositions containing such N-phosphonomethylglycine derivatives and to herbicidal methods employing such compounds and compositions.

27 Claims, No Drawings

ESTER DERIVATIVES OF N-ALKYLTHIO-N-CYCLOALKYL THIO-N-PHOSPHONOMETHYLGLYCINE AND HERBICIDAL METHODS USING SAME

This invention relates to novel ester derivatives of N-alkylthio and N-cycloalkyl thio-N-phosphonomethylglycine which are useful as herbicides and to a process for producing the same. This invention further relates to herbicidal compositions containing such N-phosphonomethylglycine derivatives and to herbicidal methods employing such compounds and compositions.

U.S. Pat. No. 4,120,689, issued to Gerard A. Dutra on Oct. 17, 1978, discloses alkyl-[di(benzyl) or di(aryl)] esters of N-phosphonomethyl glycine prepared by the reaction of a dibenzyl or diaryl phosphite with an N-methylene lower alkyl glycinate trimer. These esters and the hydrolysis products thereof containing at least one benzyloxy or aryloxy group bonded to the phosphorus atom thereof are disclosed as compounds having the formula

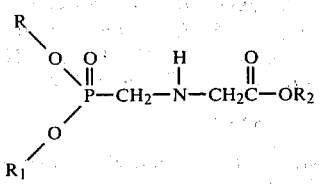

wherein R of U.S. Pat. No. 4,120,689, supra is disclosed as a member of the group consisting of phenyl, benzyl, naphthyl, biphenylyl, benzyloxyphenyl and phenyl, benzyl or naphthyl groups substituted with from 1 to 3 groups selected from the class consisting of hydroxyl, lower alkyl, lower alkoxy, lower alkylthio, trifluoromethyl, carbo (lower alkoxy), nitro or halo; $R_1$ of U.S. Pat. No. 4,120,689, supra is hydrogen or an R group, and $R_2$ of U.S. Pat. No. 4,120,689, supra is a lower alkyl group or hydrogen and the strong acid salts of the compounds wherein $R_1$ or $R_2$ is H. A post-emergent herbicide utility is disclosed.

The compounds of the present invention are represented by the formula

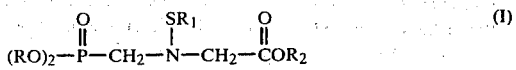

wherein R is phenyl, naphthyl or biphenylyl or phenyl, naphthyl or biphenylyl substituted with from one to three substituents independently selected from the class consisting of lower alkyl, lower alkoxy, loweralkylthio, lower alkoxycarbonyl, methylenedioxy, trifluoromethyl, cyano, nitro and halogen; and $R_1$ is alkyl or cycloalkyl and $R_2$ is lower alkyl or aralower alkyl.

It is preferred that R is phenyl.

Also, it is preferred that $R_1$ is methyl, isopropyl, or cyclohexyl and that $R_2$ is methyl, or ethyl.

As employed herein, the term "lower alkyl" designates alkyl radicals which have one to four carbon atoms in a straight or branched chain, such as, for example, methyl, ethyl, propyl, isopropyl, butyl, isobutyl, sec-butyl, and t-butyl.

The term "alkyl" designates those alkyl radicals which have one to 8 carbon atoms in a straight or branched chain.

The term "halo or halogen" as employed herein means chlorine, bromine, iodine and fluorine.

The term "lower alkoxy" includes groups representative of the term "lower alkyl" in combination with oxygen and includes methoxy, ethoxy, propoxy, butoxy mixtures thereof and the like.

The term "lower alkylthio" includes representatives of lower alkyl in combination with sulfur.

The term "lower alkoxycarbonyl" includes groups representative of the aforedefined term "lower alkoxy" in combination with a carbonyl group.

The term "cycloalkyl" is employed herein to represent carbon-hydrogen atoms arranged in a cyclic or ring arrangement having 3 to 8 carbon atoms in the ring arrangement. Typical groups representative of cycloalkyl include cyclopentyl, cyclohexyl and the like.

Illustrative of the substituted phenyl groups which R independently represents are mono-substituted phenyl wherein the substituent is in the ortho, meta or para position, for example, methylphenyl, butylphenyl, methoxyphenyl, butoxyphenyl, fluorophenyl, chlorophenyl, bromophenyl, iodophenyl, trifluoromethylphenyl, nitrophenyl, methylthiophenyl, butylthiophenyl, cyanophenyl, ethoxycarbonylphenyl, and the like, and the di- and tri-substituted phenyl groups wherein the substituents are the same or different and are located in the 2, 3, 4, 5 or 6 positions of the phenyl ring, for example dichlorophenyl, dimethylphenyl, methylchlorophenyl, ethylfluorophenyl, dibutoxyphenyl, butylnitrophenyl, methylthiochlorophenyl, di(ethylthio)phenyl, trimethylphenyl, trichlorophenyl, tributylphenyl, ethyldichlorophenyl and the like.

Groups representative of a substituted naphthyl groups represented by R include methylnaphthyl, nitronaphthyl, bromonaphthyl, dimethylnaphthyl, difluoronaphthyl, trimethylnaphthyl and the like.

Groups representative of substituted biphenylyl groups represented by R include methylbiphenylyl, nitrobiphenylyl, bromobiphenylyl, dimethylbiphenylyl, difluorobiphenylyl, trimethylbiphenylyl and the like.

In accordance with the present invention, the alkylthio-N-phosphonomethylglycine derivatives of formula (I) are prepared by reacting a compound of the formula

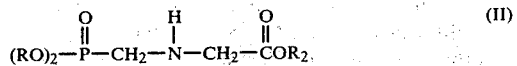

wherein R and $R_2$ are as above defined; in an aprotic solvent, with a sulfenyl chloride of the formula

wherein $R_1$ is above defined; in the presence of a hydrogen chloride acceptor.

The reaction temperature may range from about −40° to about 100° C. For ease of reaction and recovery of product, it is preferred to conduct the process of the present invention within a range of about −40° to about 30° C.

Typical sulfenyl chlorides which may be employed include those prepared by a method described in Synthesis 9, 690 (1980), Jun-ichi Ohishi, all other references described therein, which are incorporated herein in their entirety by reference.

In preparing the novel N-phosphonomethylglycine derivatives of formula (I), the ratio of reactants is not narrowly critical. For best results, however, for each mole of a compound of formula (II), one should employ one mole of a sulfenyl chloride of formula (III) to produce one mole of an N-alkylthio N-phosphonomethylglycine compound of formula (I). It is preferred to employ an excess of a sulfenyl chloride of formula (III) for ease of reaction and maximum yield of product. The hydrogen chloride acceptor is preferably used in stoichiometric excess to insure completeness of reaction.

The hydrogen chloride acceptor is an amine, preferably a tertiary amine, which will not react with the reactants or products formed. Examples of tertiary amine hydrogen chloride acceptors include trimethylamine, triethylamine, tributylamine, trihexylamine, 1,5-diazabicyclo-[5.4.0]-undec-5-ene, pyridine, quinoline and the like.

Due to the reactive nature of the various reaction intermediates and reactants, the process of the present invention should be conducted in an aprotic solvent under essentially anhydrous conditions. Illustrative of the aprotic solvents employed in the process of this invention include benzene, toluene, methylene chloride, tetrahydrofuran, cyclohexane. methylcyclohexane, hexane, octane, dioxane, ethyl and ether and the like.

While the processes of this invention can be conducted at atmospheric, sub-atmospheric or super-atmospheric pressure, for convenience and economy it is generally preferred to conduct these processes at atmospheric pressure.

The following illustrative, non-limiting examples will serve to further demonstrate to those skilled in the art the manner in which specific compounds within the scope of this invention can be prepared. In the examples, all parts are parts by weight unless otherwise expressly stated.

General Procedure For The Preparation of Alkyl And Cycloalkyl Sulfenamide Derivatives of N-Phosphonomethylglycine Triesters for

EXAMPLES I–IV

An oven-dried flask cooled under nitrogen was charged with the appropriate alkyl or cycloalkyldisulfide (about 0.02–0.04 mole) and methylene chloride and cooled to $-40°$ C. in a dry ice-acetonitrile bath. Sulfuryl chloride (1 equivalent) (either neat or as a solution in methylene chloride) was added slowly via syringe or cannual, maintaining the temperature below $-30°$ C. An immediate yellow color indicated formation of the intermediate sulfenyl chloride of formula III (2 equivalents). This reaction mixture was stirred at $-40°$ C. for 15–30 min. and transferred via cannula to a solution of the appropriate N-phosphonomethylglycine triester (about 0.02–0.04 moles) of formula (II) derivative and excess triethylamine in methylene chloride at $-40°$ C. Generally, an excess of the sulfenyl chloride was employed. The yellow reaction mixture was stirred overnight after allowing to warm slowly to room temperature. The reaction mixture was washed with cold 10% aqueous NaOH followed by cold water, dried over MgSO$_4$, filtered and concentrated in vacuo. Purification by HPLC on a Waters Prep Pak 500 silica gel column eluting with 10–50% ethyl acetate/cyclohexane gave the desired sulfenamides of formula (I) $^1$H NMR, $^{31}$P NMR and elemental analyses were consistent with pure product.

EXAMPLE I

Glycine, N-[(diphenoxyphosphinyl)methyl]-N-(methylthio)-, ethyl ester was prepared as a yellow oil corresponding to a compound of formula (I) wherein R is phenyl, R$_1$ is methyl and R$_2$ is ethyl having a refractive index of n$_D^{22.5}$=1.5449, and an analysis C$_{18}$H$_{22}$NO$_5$PS: Calculated: C,54.68; H,5.61; N,3.54; S,8.11; Found: C,54.53; H,5.61; N,3.48; S,8.15.

EXAMPLE II

Glycine, N-[(diphenoxyphosphinyl)methyl]-N-(isopropylthio)-, ethyl ester was prepared as an orange oil corresponding to a compound of formula (I) wherein R is phenyl, R$_1$ is isopropyl and R$_2$ is ethyl having a refractive index of n$_D^{22.7}$=1.5373 and an analysis: C$_{20}$H$_{26}$NO$_5$PS: Calculated: C,56.73; H,6.19; N,3.31; S,7.57; Found: C,56.47; H,6.58; N,3.12; S,7.16.

EXAMPLE III

Glycine, N-[(diphenoxyphosphinyl)methyl]-N-(cyclohexylthio)-, methyl ester was prepared as a yellow oil corresponding to a compound of formula (I) wherein R is phenyl, R$_1$ is cyclohexyl and R$_2$ is methyl, having a refracture index n$_D^{21.7}$=1.5500, having an analysis: C$_{22}$H$_{28}$NO$_5$PS: Calculated: C,58.79; H,6.28; N,3.12; S,7.13; Found: C,58.67; H,6.30; N,3.06; S,7.07.

EXAMPLE V

The post emergence herbicidal activity of some of the various compounds of this invention was demonstrated by a greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm$^2$ absolute. The atomizer contains 6 ml. of a solution of suspension of the chemical. In that 6 ml., is an amount of a cyclohexanone emulsifying agent mixture to give a spray solution or suspension which contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergence herbicidal activity index used in Table I is as follows:

| Plant Response | Index |
| --- | --- |
| 0-24% control | 0 |
| 25-49% control | 1 |
| 50-74% control | 2 |
| 75-99% control | 3 |
| 100% control | 4 |

The plant species utilized in these tests are identified by letter in accordance with the following legend:

| | |
| --- | --- |
| A - Canada Thistle* | K - Barnyardgrass |
| B - Cocklebur | L - Soybean |
| C - Velvetleaf | M - Sugar Beet |
| D - Morningglory | N - Wheat |
| E - Lambsquarters | O - Rice |
| F - Smartweed | P - Sorghum |
| G - Yellow Nutsedge* | Q - Wild Buckwheat |
| H - Quackgrass* | R - Hemp Sesbania |
| I - Johnsongrass* | S - Panicum Spp |
| J - Downy Brome | T - Crabgrass |

*Established from vegetative propagules.

A dash (-) in the tables indicates that the particular species was absent in the test.

TABLE I

| Compound of Example No. | WAT | kg/h | A | B | C | D | E | F | G | H | I | J | K |
| --- | --- | --- | --- | --- | --- | --- | --- | --- | --- | --- | --- | --- | --- |
| I | 4 | 11.2 | 2 | 4 | 4 | 3 | 4 | 4 | 3 | 4 | 4 | 3 | 4 |
|   | 4 | 5.6 | 2 | 4 | 4 | 3 | 4 | 4 | 2 | 2 | 3 | 3 | 4 |
| II | 2 | 11.2 | — | 2 | 2 | 2 | 3 | 3 | 1 | 3 | 2 | 3 | 3 |
|   | 2 | 5.6 | — | 1 | 1 | 1 | 4 | 2 | 1 | 3 | 2 | 2 | 3 |

TABLE II

| Compound of Example No. | WAT | kg/h | L | M | N | O | P | B | Q | D | R | E | F | C | J | S | K | T |
| --- | --- | --- | --- | --- | --- | --- | --- | --- | --- | --- | --- | --- | --- | --- | --- | --- | --- | --- |
| I | 4 | 5.6 | 3 | 4 | 4 | 4 | 4 | 4 | 4 | 3 | 4 | 4 | 4 | 4 | 4 | 4 | 4 | 4 |
|   | 4 | 1.12 | 2 | 4 | 4 | 3 | 3 | 3 | 3 | 3 | 3 | 4 | 4 | 4 | 3 | 4 | 4 | 4 |
|   | 4 | 0.28 | 1 | 1 | 0 | 0 | 2 | 2 | 2 | 3 | 1 | 3 | 3 | 2 | 1 | 2 | 3 | 3 |

From the test results presented in Tables I and II, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor such as ethanol mercaptan, sodium thiosulfate, dodecylmono or dimercaptan or anti-foaming agent such as a dimethylpolysiloxane, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 56.0 or more kilograms per hectare. In pre-emergent treatments, the rate of application can be from about 5.6 to about 22.4 or more kilograms per hectare. In applications for the control of aquatic plants, the active ingredients are applied in amounts of from about 1.0 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

There are several possible methods for applying liquid compositions of this invention to emerged plants. Such methods include the use of wiper systems whereby the plant to be treated is contacted with an absorbent material containing the particular liquid composition, a portion of which is thereby released onto the plant upon contact therewith. Such wiper systems typically comprise a reservoir of the liquid composition into which a portion of the absorbent material is placed and is fed therethrough. Generally, substances employable as absorbent material include substances of any shape or form capable of absorbing the liquid composition and releasing a portion of the same upon contact with the plant. Typical absorbent materials include felt, foam rubber, cellulose, nylon, sponges, hemp, cotton, burlap, polyester over acrylic, combinations thereof and the like. Forms of absorbent material include rope, twine, string, cloths, carpets, combinations thereof and the like. These forms may be assembled in any manner desired including a pipe rope wick, a wedge rope wick, a multi-rope wick and the like.

In another possible application method, liquid compositions may be selectively applied to weeds by the use of recirculating sprayer systems wherein the recirculating spray unit is mounted on a tractor or high clearance mobile equipment and the spray is directed horizontally onto the weeds growing over a crop. Spray not intercepted by the weeds is collected in a recovery chamber before contacting the crop and is reused. Roller applications may also be employed to apply liquid compositions to weeds growing over a crop.

In yet another possible application method, shielded applicators may be employed to direct the liquid composition in the form of a spray onto the weeds while effectively shielding the crops from the spray.

These and other possible application methods for selectively applying liquid compositions to weeds are discussed in detail in Innovative Methods of Post-Emergence Weed Control, McWhorter C. G., Southern Weed Science Society, 33rd Annual Meeting Proceedings, Jan. 15–17, 1980; Auburn University Printing Service, Auburn, Ala. U.S.A., the teachings of which are incorporated herein by reference in their entirety.

Another possible method of applying liquid compositions of this invention to plants includes controlled droplet application which is also known as the ultra low-volume chemical application. Controlled droplet application involves the production of uniform or nearly uniform spray drops of a predetermined size and the conveyance of these drops with negligible evaporation to a spray target. In particular, this method comprises feeding spray solutions to a rotary atomizer comprising a small disk with serrated edges that disperses liquid into droplets as the disk spins. Different droplet sizes are produced by changing solution flow rates to the spinning disk or changing the speed of rotation of the disk.

Those of skill in the art will recognize that the physical and chemical characteristics of the compound or composition employed will determine to a large extent the particular application method selected therewith.

The aforementioned and other methods for applying liquid compositions to plants are discussed in detail in "Rope Wick Applicator-Tool With A Future", Dale, James E., pp. 3–4, "The Recirculating Sprayer and Roundup/Herbicide", Derting, Claude W., pp. 5–7, and "C.D.A. Herbicide Application", McGarvey, Frank X., *Weeds Today*, Volume 11, Number 2, pp. 8–9, Late Spring, 1980, 309 W. Clark St., Champaign, Ill., the teachings of which are incorporated herein by reference in their entirety.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method for controlling undesired plants which comprises contacting said plants or plant growth medium with a herbicidal amount of a compound of the formula

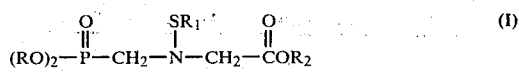

wherein R is phenyl, naphthyl or biphenylyl or phenyl, naphthyl or biphenylyl substituted with from one to three substituents independently selected from the class consisting of lower alkyl, lower alkoxy, loweralkylthio, lower alkoxycarbonyl, methylenedioxy, trifluoromethyl, cyano, nitro and halogen; and $R_1$ is alkyl or cycloalkyl and $R_2$ is alkyl or aralower alkyl.

2. A method according to claim 1 wherein R is phenyl and $R_2$ is alkyl or aralower alkyl.

3. A method according to claim 2 wherein said compound is Glycine, N-[(diphenoxyphosphinyl)methyl]-N-(methylthio)-, ethyl ester.

4. A method according to claim 2 wherein said compound is Glycine, N-[(diphenoxyphosphinyl)methyl]-N-isopropylthio)-, ethyl ester.

5. A method according to claim 2 wherein said compound is Glycine, N-[(diphenoxyphosphinyl)methyl]-N-(cyclohexylthio)-, methyl ester.

6. A compound of the formula

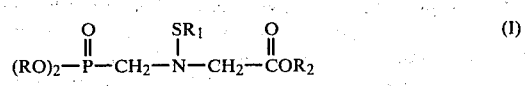

wherein R is phenyl, naphthyl or biphenylyl or phenyl, naphthyl or biphenylyl substituted with from one to three substituents independently selected from the class consisting of lower alkyl, lower alkoxy, loweralkylthio, lower alkoxycarbonyl, methylenedioxy, trifluoromethyl, cyano, nitro and halogen; and $R_1$ is alkyl or cycloalkyl and $R_2$ is alkyl or aralower alkyl.

7. A compound according to claim 6 wherein R is phenyl and $R_2$ is alkyl or aralower alkyl.

8. A compound according to claim 7 wherein said compound is Glycine, N-[(diphenoxyphosphinyl)methyl]-N-(methylthio)-, ethyl ester.

9. A compound according to claim 7 wherein said compound is Glycine, N-[(diphenoxyphosphinyl)methyl]-N-(isopropylthio)-, ethyl ester.

10. A compound according to claim 7 wherein said compound is Glycine, N-[(diphenoxyphosphinyl)methyl]-N-(cyclohexylthio)-, methyl ester.

11. A herbicidal composition comprising an inert adjuvant and a herbicidally effective amount of a compound of the formula

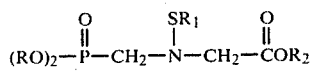  (I)

wherein R is phenyl, naphthyl or biphenylyl or phenyl, naphthyl or biphenylyl substituted with from one to three substituents independently selected from the class consisting of lower alkyl, lower alkoxy, loweralkylthio, lower alkoxycarbonyl, methylenedioxy, trifluoromethyl, cyano, nitro and halogen; and $R_1$ is alkyl or cycloalkyl and $R_2$ is alkyl or aralower alkyl.

12. A composition according to claim 11 wherein R is phenyl and $R_2$ is alkyl or aralower alkyl.

13. A composition according to claim 12 wherein said compound is Glycine, N-[(diphenoxyphosphinyl)methyl]-N-(methylthio)-, ethyl ester.

14. A composition according to claim 12 wherein said compound is Glycine, N-[(diphenoxyphosphinyl)methyl]-N-(isopropylthio)-, ethyl ester.

15. A composition according to claim 2 wherein said compound is Glycine, N-[(diphenoxyphosphinyl)methyl]-N-(cyclohexylthio)-, methyl ester.

16. A process for preparing a compound of the formula

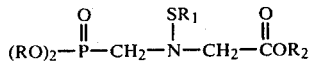

wherein R is phenyl, naphthyl or biphenylyl or phenyl, naphthyl or biphenylyl substituted with from one to three substituents independently selected from the class consisting of lower alkyl, lower alkoxy, loweralkylthio, lower alkoxycarbonyl, methylenedioxy, trifluoromethyl, cyano, nitro and halogen; and $R_1$ is alkyl or cycloalkyl and $R_2$ is alkyl or aralower alkyl which comprises reacting a compound of the formula

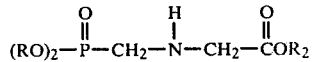

wherein R and $R_2$ are as above defined in an aprotic solvent with a sulfenyl chloride of the formula

wherein $R_1$ is as above defined in the presence of a hydrogen chloride acceptor.

17. The process of claim 16 wherein said aprotic solvent comprises benzene, toluene, tetrahydrofuran, methylene chloride, cyclohexane, methylcyclohexane, hexane, octane, dioxane, ethyl ether and mixtures thereof.

18. The process of claim 17 wherein said aprotic solvent comprises methylene chloride.

19. The process of claim 18 wherein said hydrogen chloride acceptor is an amine.

20. The process of claim 19 wherein said amine is a tertiary amine.

21. The process of claim 20 wherein said amine is triethylamine.

22. The process of claim 21, wherein the temperature of said reaction is in the range from about −40° C. to about 100° C.

23. The process of claim 22, wherein the temperature of said reaction is in the range from about −40° C. to about 30° C.

24. The process of claim 23, wherein R is phenyl and $R_2$ is alkyl or aralower alkyl.

25. The process of claim 24, wherein $R_1$ is methyl and $R_2$ is ethyl.

26. The process of claim 24, wherein $R_1$ is isopropyl and $R_2$ is ethyl.

27. The process of claim 24, wherein $R_1$ is cyclohexyl and $R_2$ is methyl.

* * * * *